United States Patent [19]

Tuerkheimer et al.

[11] Patent Number: 4,721,124
[45] Date of Patent: Jan. 26, 1988

[54] OPTOMETRIC SOFT AND RIGID CONTACT LENS CLEANING AND STORAGE SYSTEM

[76] Inventors: Barry Tuerkheimer, 238 S. University Dr., Plantation, Fla. 33324; Robert Cranmore, 815 NW. 57th St., Ft. Lauderdale, Fla. 33309

[21] Appl. No.: 556,973

[22] Filed: Dec. 1, 1983

[51] Int. Cl.⁴ ............................................... B08B 3/02
[52] U.S. Cl. ...................................... 134/138; 134/135; 134/143; 134/147; 134/200; 206/5.1
[58] Field of Search .................... 134/86, 89, 92, 117, 134/135, 137, 138, 139, 143, 147, 148, 149, 153, 157, 162, 196, 197, 201, 200; 15/214; 206/5.1, 5; 68/96, 213; 239/327, 373

[56] References Cited

U.S. PATENT DOCUMENTS

| | | |
|---|---|---|
| 1,143,217 | 6/1915 | McGarth . |
| 1,962,376 | 6/1934 | Zarobsky . |
| 2,062,704 | 12/1936 | Forsyth . |
| 2,203,479 | 6/1940 | Witwer et al. . |
| 2,641,170 | 6/1953 | Hutchins . |
| 2,712,826 | 7/1955 | Schleyer et al. . |
| 2,721,567 | 10/1955 | Tierney . |
| 2,823,682 | 2/1958 | Coulter . |
| 3,041,212 | 6/1962 | Booth ........................... 134/138 X |
| 3,066,687 | 12/1962 | Rohmann ..................... 134/148 |
| 3,113,579 | 12/1963 | Willis . |
| 3,139,097 | 6/1964 | Hungerford et al. . |
| 3,139,098 | 6/1964 | Hungerford et al. . |
| 3,140,647 | 7/1964 | Miller . |
| 3,167,079 | 1/1965 | Weil . |
| 3,343,657 | 9/1967 | Speshyock ................... 206/5.1 |
| 3,379,200 | 4/1968 | Pennell . |
| 3,444,868 | 5/1969 | Hungerford et al. ........ 134/143 |
| 3,567,064 | 3/1971 | Churan . |
| 3,586,012 | 6/1971 | Paule . |
| 3,621,855 | 11/1971 | Rabinowitz .................. 206/5.1 |
| 3,623,492 | 11/1971 | Frantz . |
| 3,643,672 | 2/1972 | Brown .......................... 134/143 |
| 3,770,113 | 11/1973 | Thomas ....................... 134/143 X |
| 3,894,551 | 7/1975 | Stohlman .................... 134/117 X |
| 3,939,968 | 2/1976 | Ryder .......................... 206/5.1 |
| 4,009,777 | 3/1977 | Thomas . |
| 4,223,782 | 9/1980 | Giambalvo ................... 206/5.1 |
| 4,396,583 | 8/1983 | LeBoeuf ...................... 206/5.1 |
| 4,444,307 | 4/1984 | Jermyn ........................ 206/5.1 |

FOREIGN PATENT DOCUMENTS

| | | |
|---|---|---|
| 458864 | 4/1928 | Fed. Rep. of Germany . |
| 1011412 | 6/1952 | France . |
| 1197161 | 7/1970 | United Kingdom ............ 205/5.1 |

Primary Examiner—Harvey C. Hornsby
Assistant Examiner—Frankie L. Stinson
Attorney, Agent, or Firm—Dickstein, Shapiro & Morin

[57] ABSTRACT

A system for storing, cleaning, and sterilizing soft and rigid contact lens. The system utilizes the circulation of cleaning fluid to clean lens which are suspended. The system consists of a container for housing a pair of off-set lens carriers and for functioning as a chamber for cleaning and sterilizing; a cap with apertures for providing a generally water-tight seal for the container and for supporting the lens carriers, and a base/pump housing connected to the bottom of the container for retaining the cleaning fluid and providing a pump mechanism for propelling the cleaning fluid into the cleaning chamber. The container has a floor with a plurality of angled apertures for providing a helically shaped spray of cleaning fluid onto the lens carriers upon manipulation of the base and pump housing. The base/pump housing attached to the bottom of the container is a flexible housing for storing the cleaning fluid and for providing a pump mechanism upon compression for forcing the cleaning fluid through the angled apertures into the cleaning chamber. An interior vessel is provided for water-tight attachment with the cover within the cleaning chamber to retain the two lens carriers side by side during storage. The lens carriers consist of two generally parallel mesh concave surfaces for retaining the contact lens. The mesh surface has a plurality of openings for allowing impact of cleaning fluid onto the retained contact lens. An electrically driven pump actuator may be utilized to cyclically compress the base and pump housing for irrigating the retained lens for a specified period of time.

4 Claims, 9 Drawing Figures

U.S. Patent  Jan. 26, 1988  4,721,124
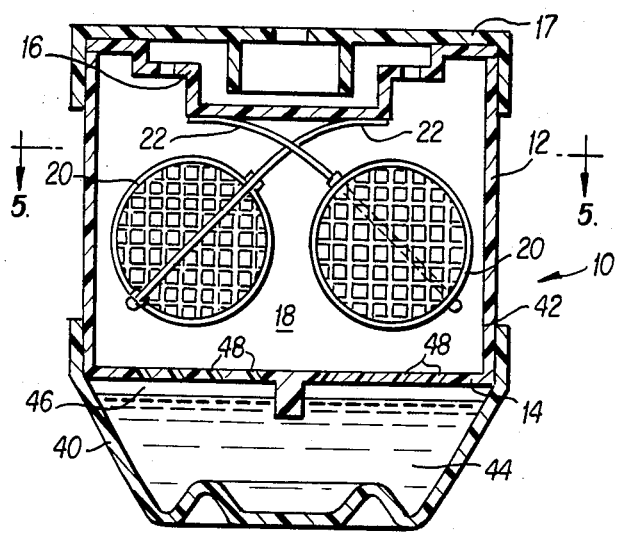
FIG. 1
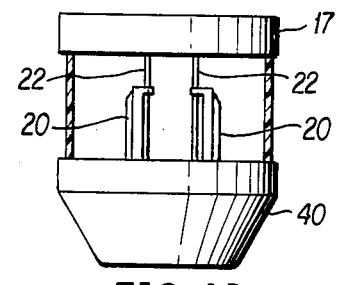
FIG. 1A
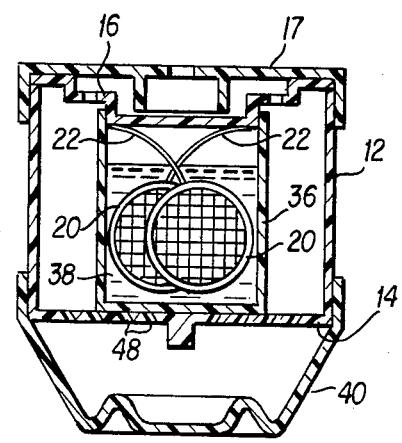
FIG. 2
FIG. 2A
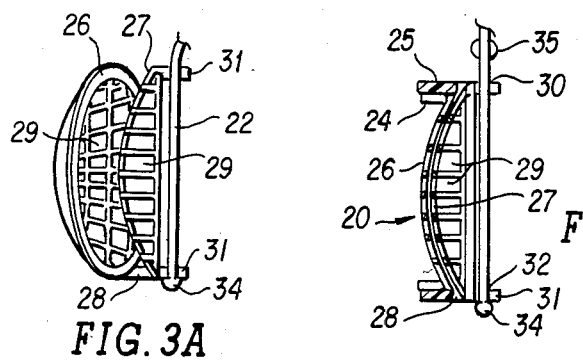
FIG. 3A  FIG. 3
FIG. 4
FIG. 5
FIG. 6

OPTOMETRIC SOFT AND RIGID CONTACT LENS CLEANING AND STORAGE SYSTEM

BACKGROUND OF THE INVENTION

The disclosed invention presents a new, unique and original method for improved cleaning, sterilizing and storage of commonly used soft or rigid contact lens. The instant invention regulates dosage of solution to comply with cleaning requirements. This device overcomes many of the existing problems and inconveniences which result from multiple handling and ineffective cleaning which results from systems presently available to users. A typical problem is the frequent tearing of soft lens which results from excessive or improper handling by the user. Another problem with existing manual systems is that particles may become imbedded in the lens during manual washing. Also hand washing can be ineffective due to variations in the procedure by the user or lack of compliance with cleaning requirements. Damage may result to the lens as a result of the physical contact by miniscule particles during hand washing, resulting in scarring of the lens. By reducing the amount of handling by the user there is less chance of dropping the lens and contaminating or damaging it. Another significant advantage is the fact that since washing the lens becomes easier as a result of the present invention, the user will more readily comply with the cleaning requirements thereby reducing injury to the eye as a result of dirty lens. As a result of improper washing or contamination of the lens, infection of the eye may occur. With the increased populatity and use of soft contact lens there has occurred an epidemic of giant papillary conjunctivitis resulting from the dirty lenses. Also a reduction in the tedious procedure of washing will encourage more people to attempt to use contact lens who are now discouraged by the presently available cleaning methods. The problem of ineffective or incomplete cleaning of the lens by the present hand cleaning method, is overcome by the present invention by retaining the lens within the lens carrier during cleaning and by providing for cleaning of the lens by irrigation as a result of the recirculation of cleaning fluid within a confined and closed cleaning chamber by the manual or mechanical compression of the resilient chamber compelling cleaning fluid into the cleaning chamber by the base/pump housing through angled or otherwise situated apertures in the cleaning chamber structure. The lens carriers are rotatably attached to the support strands so that they will rotate about the support strands upon impact by a plurality of streams of the cleaning solution thereby ensuring overall exposure of the lens to the cleaning fluid streams. An interior accessory vessel may be utilized for longer term storage, soaking or sterilization of the lens within the lens carriers.

In one embodiment a plurality of angled apertures in the structure of the cleaning chamber produce a plurality of individual streams of fluid to create a helically shaped spray of cleaning fluid impacting onto the lens carriers causing them to rotate about the support strands improving the irrigation circulation of cleaning fluid on the lens. An electrically driven pump actuator may be utilized for automatic manipulation of the pumping unit and cleaning of the lens.

The instant invention provides easy portability and convenience of use with cleaning solutions of various viscosities and chemical compositions. Solution and lens may be left in storage in the unit and may be transported during storage without spillage or contamination until the lens are next worn.

OBJECTIVES OF THE INVENTION

It is an objective of the invention to provide a device that cleans hard or soft contact lenses by circulation of cleaning fluid to irrigate the lens' surface.

Another objective of the invention is to provide a device for circulating the cleaning fluid within a cleaning chamber.

Yet another objective of the invention is to provide a device for circulating fluid in directed streams to form a spray to impact on the surface of the lenses.

Still another objective of the invention is to provide a spray of cleaning fluid which is helical in shape.

Yet another objective of the invention is to provide a helical spray of cleaning fluid upward from the floor of the cleaning chamber.

Still another objective of the invention is to provide a plurality of apertures for producing angled curved streams of cleaning fluid to form a helical spray.

Yet still another objective of the invention is to provide a cleaning system having a cleaning chamber and a pump/storage chamber for containing the cleaning fluid.

Another objective of the invention is to provide a cleaning system having a resilient pump section which can be manually compressed to create a supply of pressurized cleaning fluid to the cleaning chamber.

Still another objective of the invention is to provide a cleaning system having a means for retaining the lenses in their normal curved configuration and to expose the surfaces of the lens to the circulating cleaning fluid.

Yet another objective of the invention is to provide a cleaning system having the lens retaining means suspended within the cleaning chamber by support means to provide exposure of the lenses to the spray of cleaning fluid.

Another objective of the invention is to provide a cleaning system wherein the lens retaining means rotate about the support means to expose all surfaces of the lenses to the spray of cleaning fluid.

An objective of the invention is to provide a cleaning system having an electrically driven compressor to cylically compress the pump means for cleaning the lenses.

BRIEF DESCRIPTION OF THE INVENTION

The instant invention consists primarily of a container which has two chambers for cleaning and storage, an inner cleaning chamber and another chamber for storage of the fluid. A cover for the container is provided retaining the support strands for rotatably suspending the lens carriers. The cover attaches to the container for a water-tight connection but provides apertures within the cap for allowing air to escape from the cleaning chamber during the compression or washing cycle and any fluid to drip back into the cleaning chamber. The lens carriers are suspended from the cap by the support strand into the cleaning chamber and are positioned generally parallel and offset from one another within the cleaning chamber. This offset positioning allows each lens carrier to rotate about the end of its support strand. A resilient base/pump housing is connected to the bottom of the container. Cleaning solution is placed in the base/pump housing so that it is almost flush with the floor of the container. The floor or other portion of the strucutre of the cleaning chamber of the container has a plurality of apertures so that when the cleaning fluid is forced through the apetures upon manipulation of the base/pump housing it provides a spray of fluid which impacts on the lenses. In one embodiment the apetures are situated in the floor and are angled to provide a helically shaped spray of cleaning fluid will provide for cleaning by circulation of the fluid causing irrigation of the lens by impact and splashing on the lens in the carrier. The ideal impact angle of the spray on the lens is 90 degrees to the plane of the surface, however, the rotation of the carrier and angle of the spray will result in a plurality of impact angles. The various-angled impacting spray, however, will provide efficient irrigation of the lens for cleaning, even during rotation. The rotation of the carrier will provide increased exposure of the lens surface to the spray. This impact of the helically shaped spray will cause the lens carrier to rotate about the support strand so that all surfaces of the lens retained within the lens carrier are exposed to irrigation thereby improving the washing. The cleaning and irrigation action is instituted by compressing the flexible base/pump housing forcing the liquid therein through the angled apertures into the cleaning chamber. Air is released through the apertures in the cover to allow the fluid to be injected into the cleaning chamber by the force of the compression of the base/pump housing. Upon release of compression on the base/pump the flexible housing will return to its original shape and allow the fluid to drain from the cleaning chamber back into the base/pump housing for the next cycle of compression and irrigation. Also in the floor-apeture embodiment fluid which may have been compelled into and onto the cover will drip down onto the lens and then into the storage container.

DESCRIPTION OF THE DRAWINGS

FIG. 1 is a front elevational cross sectional view of the invention.

FIG. 1A is a side, partial cut away of the invention showing the lens carriers suspended within the cleaning chamber.

FIG. 2 is a front elevational cross section of the invention with the interior storage vessel installed.

FIG. 2A is a perspective view of the interior vessel.

FIG. 3 is a side elevational view of a lens carrier.

FIG. 3A is a side elevational view of the lens carrier in the open position.

FIG. 4 is a side elevational view of the cover of the invention with supporting strands for the lens carrier.

FIG. 5 is an overhead cross sectional view of the cleaning chamber showing the location of the angled apertures and lens carrier.

FIG. 6 is a side elevational view of the electrically driven manipulator for compressing the pump housing.

PREFERRED EMBODIMENT OF THE INVENTION

In FIG. 1 the contact lens cleaning, sterilizing and storage system is shown generally as number 10. The system 10 consists of an outer container 12 which may be circular in shape as shown in FIG. 5. The container 12 is open at the top and has a floor 14. A cover 16 is provided for the top opening of container 12 which is secured to container 12 by a cap 17 with a snap connection as shown in FIG. 1 to provide a generally water-tight fit. Within the container 12 is defined a cavity, cleaning chamber 18, for housing a pair of lens carriers 20 which is suspended from the cover 16 by connection with two support strands 22 extending downward from the cover 16 into the cleaning chamber 18 for connection with the lens carrier 20. A lens carrier 20 is rotatably connected to the end of each strand 22 which is connected to cover 16 (generally during molding) so that the pair of lens carriers 20 are generally parallel but offset from each other so that each might rotate about their respective support strand 22 freely without contact with the other lens carrier (as shown in FIG. 5). A lens carrier consists of two sections 24 and 25 having two generally parellel concave open mesh surfaces 26 and 27 which are connectable for retaining either the soft or rigid contact lens (not shown) between them. Surface 26 is a part of section 24 and surface 27 is a part of section 25. The two carrier sections 26 and 27 are connected by a hinge means 28 so that they may be easily opened and closed to facilitate insertion and removal of the lens. The hinge means 28 will be a segment of material connecting sections 24 and 25 which is flexible to allow bending for opening and closing the sections of the carrier. Such hinges are well known in the art known by the title "living hinge". The two sections 24 and 25 of each carrier are curved so as to accomodate the curvature of the lens between them when in the closed position (shown in FIG. 3). These carriers are connected on the ends of each flexible support strand 22 by a common snap on connection 31 well known in the art at 30 and 32 in such a way as to permit the carrier 20 to rotate about the strand as shown in FIGS. 1, 1A, 3 and 5—each carrier 20 being positioned to permit its rotation without interference with the other carrier's rotation when in the cleaning mode. A ball 34 is provided on each end of the strand 22 to prevent the lens carrier 20 from sliding off the strand. A bulb 35 may be placed (molded) above the carrier 20 on strand 22 to prevent movement of the carrier along the strand 22. Carrier surface 26 and 27 have a plurality of opening 29 to permit the entry of the spray of fluid onto the lens surface held between surfaces 26 and 27. These openings are readily seen in carrier 20 in FIGS. 1, 2 and 3. In a storage mode an inner vessel 36 (FIGS. 2 and 2A), able to fit within cleaning chamber 18, is filled to a level with a prescribed cleaning or sterlizing solution. Both lens carriers 20 are manipulated on the resilient flexible support strand 22 so that they are now parallel and adjacent as shown in FIG. 2 to fit within the inner vessel 36, which is smaller than the cleaning chamber of the system in order to reduce the amount of fluid required. the inner vessel is shaped for a snap-in water-tight connection with a portion of the cover 16 as shown in FIG. 2. When the lenses are ready for use the inner vessel may be removed and the liquid 38 therein discarded. At this time the lens retained within the lens carrier may be recleaned, sterilized or rinsed, as appropriate.

As shown in FIG. 1 the system has a base/pump housing 40 attached in water-tight connection with the bottom portion 42 of the container 12. This housing 40 is resilient and flexible so that it may be compressed inward toward the container 12 to propel fluid 44 from its hollow inner chamber 46 through a plurality of apertures 48 in the floor 49 or even walls or top of container 12 into the cleaning chamber 18 and onto the lens. The embodiment showing the use of apetures in the structure of container 12 (other than the floor 49) is not shown, however, it would be simple to provide a container 12 with passageways in the walls or other means of communicating the fluid to apertures in the walls or cover of Container 12. The apertures would provide a directed stream of solution to effect the circulation and recirculation of fluid within the cleaning chamber to irrigate the lenses. Perhaps the simpler and more practical embodiment is the use of apertures in the floor as shown in the drawings. FIG. 1 is a cross sectional elevational view of the system 10 showing the lens carriers 20 suspended in their cleaning position, prepared for the washing phase. As shown, the base/pump housing 40 is filled with an appropriate cleaning solution 44. FIG. 1A shows another view of the lens carriers 20 within the cleaning chamber 18 showing their parallel but offset positions which allows rotation about strand 22 upon impact of the fluid.

FIG. 2 shows the system 10 with the inner vessel 36 (FIG. 2A) installed within the cleaning chamber 18 for storage of the lens carriers 20 within a solution. The inner vessel 36 is in water-tight connection with the cover 16 by a common snap on connection. The lens carriers have been manipulated on their support strand to a parallel and adjacent position to fit within the reduced cavity of the inner vessel 36. This is possible due to the flexible nature of the support strands of the lens carriers and their offset positioning.

FIG. 2 shows the lens carriers 20 stored within the inner vessel 36 within the container 12.

FIGS. 3 and 3A shows the two generally parallel concave sections 26 and 27 of lens carrier 20. These two sections are in hinged connection so that they might be open and closed for insertion and removal of the lens. The generally curved and parallel oval surfaces 26 and 27 of the two sections 24 and 25 provide a gap for retention of the curved contact lens. The lens carrier 20 is rotatably connected to the support strand 22 by common snap on connection 31. Strand 22 snaps into a generally c-shaped segment of connection 31 and although retained there by impinging contact strand 22, is rotatable within the c-shaped segment for rotation upon impact by the helical spray of fluid resulting from the plurality of angle streams of fluid ejecting from each aperture 48. Lens carrier 20 has a plurality of openings 29 in the oval surfaces so that the surfaces of the retained lens are exposed to contact with the spray of cleaning fluid for cleaning by irrigation.

FIG. 3A shows the lens carrier 20 in the open position.

FIG. 4 shows the cover 16 with the flexible support strands extending downward.

FIG. 5 shows an overhead view of the lens carriers 20 within the cleaning chamber 18 positioned above the floor 49 of the container 12. The floor 49 has a plurality of apertures 48 which are positioned at such an angle as to provide a helical shaped spray of cleaning fluid upward onto the lens carriers 20 upon manipulation and compression of the base/pump housing 40. These streams 50 (shown by arrows in FIG. 5) of fluid will impact upon the lens carrier 20 as shown in FIG. 5 much like the sprayer within a dishwasher, thereby impacting the lens carriers causing them to rotate about the strand 22. This rotation of the lens carriers will be compelled and sustained by the cyclic spray of water provided by the cyclic manipulation of the base/pump housing. In this fashion the lens carriers are caused to continuously rotate about the support strand during the washing operation thereby exposing the entire surface of the lens to be cleaned to irrigation by the circulation of cleaning solution. In this manner the instant invention provides for complete circulation, irrigation and cleaning of the contact lens.

FIG. 6 shows an electrically driven device 54 for compressing housing 40 to inject the cleaning fluid into cleaning chamber 18. Platform 52 is cyclically driven upwards to compress housing 40. This device 54 will perform the manual compression electrically which is normally done by the user manually with his hand and finger cyclically compressing housing 40.

What I claim is:

1. A system for storing, cleaning and sterilizing soft and rigid contact lenses, comprising:

a container having an internal cavity, a floor with apertures, and an upper opening;

a cover connectable over said upper opening having a generally water-tight connection, said cover having means for releasing air from said internal cavity;

one or more carriers connected to said cover and rotatably suspended above said floor within said cavity, said carrier having at least one pair of generally parallel concave surfaces hinged together, and said pair of surfaces connectable forming a concave cavity generally curved to the shape of the contact lens, the contact lens retainable within said concave cavity;

a pump/base housing having a compressible and resiliently expandable outer surface and a storage capacity, said housing having a connectable, generally water-tight attachment to a bottom portion of said container, said cavity in fluid communication with said internal cavity of said container through said aperture in said floor, said apertures being formed such that fluid directed therethrough into said internal cavity will impact on said contact lens to cause said contact lens and said carrier to rotate.

2. A storage, cleaning and sterilization system for soft and rigid contact lenses, comprising:

a lens supporting means for retaining one or more contact lens exposed to circulating fluid for cleaning by irrigation;

a cleaning means connected to said lens supporting means for cleaning said lens through irrigation of the lens by circulation of a cleaning fluid within said cleaning means;

said cleaning means including an irrigation means, said irrigation means connected to said lens supporting means in fluid communication for providing cyclic circulation of the fluid into said lens supporting means to impact onto the contact lens in said lens supporting means;

said irrigation means including a pump means and a fluid circulating means, said pump means connected to said lens supporting means in fluid communication for cyclically providing a quantity of the fluid under pressure to said fluid circulating means, said fluid circulating means connected to said pump means in fluid communication for providing circulation of directed streams of pressurized fluid in a helical shape onto said lens supporting means to impact onto the contact lens in said lens supporting means;

said circulating means including a fluid directing means in fluid communication with said lens supporting means connected to said pump means in fluid communication for directing a spray of a plurality of directed streams of fluid onto the lenses;

said fluid directing means including a plurality of angled aperture means in a floor of said cleaning means for providing a plurality of streams of upwardly propelled fluid forming a helically shaped spray impacting upon the contact lens in said lens storage means and said fluid directing means providing for drainage of said fluid back into said pump means during resilient expansion of said housing means.

3. A storage, cleaning and sterilization system for soft and rigid contact lenses, comprising:

a lens supporting means for retaining one or more contact lens rotatably disposed and exposed to circulating fluid for cleaning by irrigation;

a cleaning means connected to said lens supporting means for cleaning said lens through irrigation of the lens by circulation of a cleaning fluid within said cleaning means, said cleaning fluid being directed in streams to impact on the surface of said lens to effect the cleaning of said lens and to cause rotation of said lens so that essentially the entire surface of said lens is exposed to the washing effect of said streams;

said cleaning means includes an irrigation means, said irrigation means connected to said lens supporting means in fluid communication for providing cyclic circulation of the fluid into said lens supporting means to impact onto the contact lens in said lens supporting means; and said pump means includes a compressible resilient housing means in a generally water-tight connection to said lens cleaning means in fluid communication with said housing means for providing storage of said fluid and cyclic propulsion of said fluid through said fluid directing means by compression and resilient expansion of said housing means.

4. A storage, cleaning and sterilization system for soft and rigid contact lenses, comprising:

a lens supporting means for retaining one or more contact lens rotatably disposed and exposed to circulating fluid for cleaning by irrigation;

a cleaning means connected to said lens supporting means for cleaning said lens through irrigation of the lens by circulation of a cleaning fluid within said cleaning means, said cleaning fluid being directed in streams to impact on the surface of said lens to effect the cleaning of said lens and to cause rotation of said lens so that essentially the entire surface of said lens is exposed to the washing effect of said streams;

said cleaning means includes an irrigation means, said irrigation means connected to said lens supporting means in fluid communication for providing cyclic circulation of the fluid into said lens supporting means to impact onto the contact lens in said lens supporting means;

said irrigating means includes a pump means and a fluid circulating means, said pump means connected to said lens supporting means in fluid communication for cyclically providing a quantity of the fluid under pressure to said fluid circulating means, said fluid circulation means connected to said pump means in fluid communication for providing circulation of directed streams of pressurized fluid in a helical shape onto said lens supporting means to impact onto the contact lens in said lens supporting means;

said circulating means includes a fluid directing means in fluid communication with said lens supporting means connected to said pump means in fluid communication for directing a spray of a plurality of directed streams of fluid onto the lenses;

said pump means includes a compressible resilient housing means in a generally water-tight connection to said lens storage means in fluid communication;

said housing means for providing storage of said fluid and cyclic propulsion of said fluid onto said fluid directing means by manual compression and resilient expansion of said housing means; and said fluid directing means includes a plurality of angled aperture means in a floor of said cleaning means for providing a plurality of streams of upwardly propelled fluid forming a helically shaped spray impacting upon the contact lens in said lens supporting means and said fluid directing means providing for draining of said fluid back into said pump means during resilient expansion of said housing means.

* * * * *